United States Patent [19]
Acorn et al.

[11] Patent Number: 5,297,558
[45] Date of Patent: Mar. 29, 1994

[54] ALGORITHM FOR PRESCRIBING AN EXERCISE REGIMEN TO ENHANCE FAT BURNING AND CARDIOVASCULAR FITNESS

[75] Inventors: Russell G. Acorn; Michael G. Tyler, both of White Bear Lake; David B. Viele, Shoreview, all of Minn.

[73] Assignee: Medical Graphics Corporation, St. Paul, Minn.

[21] Appl. No.: 30,685

[22] Filed: Mar. 12, 1993

[51] Int. Cl.$^5$ .............................................. A61B 5/08
[52] U.S. Cl. .................................... 128/719; 128/700; 128/707
[58] Field of Search ............... 128/719, 700, 726, 671, 128/707

[56] References Cited

U.S. PATENT DOCUMENTS 3,895,630 7/1975 Bachman .............................. 73/23 R
4,463,764 8/1984 Anderson et al. .................... 128/719

OTHER PUBLICATIONS

"Online Computer for Assessing Respiratory and Metabolic Function During Exercise" Medical & Biological Engineering & Computing, May 1981, pp. 340–348.

*Primary Examiner*—William E. Kamm
*Assistant Examiner*—Scott M. Getzow
*Attorney, Agent, or Firm*—Haugen and Nikolai

[57] ABSTRACT

A method for optimizing either fat utilization or cardiovascular performance during an exercise regimen includes the steps of using a cardiovascular exercise system to measure a subject's respiratory exchange ratio on a breath-by-breath basis and also locating the subject's anaerobic threshold. By locating a fat burning point as the point where the RER is a minimum less than 0.90 at a time when oxygen uptake is less than 55 percent of the peak oxygen uptake and then correlating that fat burning point with the existing heart rate, a fat burning zone can be established by taking that heart rate and adding and subtracting 10 percent from it. The work rate at the target heart rate can also be used to determine the zone. For enhanced cardiovascular performance training, the heart rate existing at the subject's anaerobic threshold is determined and it is set as the lower boundary for a zone whose upper boundary is that value plus 20 percent. The corresponding work rate at these heart rates can also be used to determine the zone.

5 Claims, 3 Drawing Sheets

ALGORITHM FOR PRESCRIBING AN EXERCISE REGIMEN TO ENHANCE FAT BURNING AND CARDIOVASCULAR FITNESS

BACKGROUND OF THE INVENTION

I. Field of the Invention

This invention relates generally to a method for prescribing an exercise regimen for a particular subject, and more particularly to a method for correlating a heart rate or work rate to be maintained throughout an exercise session if the desired goal of the exercise is to reduce fat or to improve cardiovascular performance

II. Discussion of the Prior Art

It is well recognized that frequent exercise is beneficial to most individuals so long as it is properly engaged in, taking into account the individual's own physiologic condition It is important that the exercise regimen not be so intensive that it adversely affects the general well being of the subject, yet not too light that it provides little or no benefit.

It is well understood that with increasing exercise, muscles need to burn metabolic fuels to perform mechanical work Carbohydrates and fat are the typical sources of fuel and must be oxidized, using molecular $O_2$ from the atmosphere to effectively provide energy. A normal response to exercise is to increase the blood flow to the working muscles which carries oxygen and removes carbon dioxide, the bi-product of biologic metabolism. The increasing demands for oxygenated blood are met by increasing the cardiac output (increased heart rate and increased stroke volume) and redistributing the blood flow to the working muscles and away from the abdominal area.

As a consequence of the need for more oxygen and the increased production of carbon dioxide, the level of ventilation must also increase. More air is taken in, in order to oxygenate the increased amount of blood going through the lungs and to eliminate the increased amount of carbon dioxide being brought to the lungs from the working muscles Ventilation normally increases in direct linear fashion with $CO_2$ output rather than oxygen uptake ($\dot{V}O_2$) such that the arterial carbon dioxide tension remains constant during aerobic work.

The heart rate also increases in a linear fashion with increasing $\dot{V}O_2$ and the maximum heart rate is limited in any individual by age.

When the supply of oxygenated blood falls short of the oxygen needs of the muscles, anaerobic metabolism ensues. The bi-product of anaerobic metabolism is lactic acid, which is buffered by the bicarbonate system. Additional $CO_2$ is produced which must be eliminated by the lungs to keep arterial carbon dioxide tension from rising. Carbon dioxide output ($\dot{V}CO_2$) will be increased relative to $\dot{V}O_2$. This will be seen in graphic form as an increase in $CO_2$ output and ventilation with respect to oxygen uptake. Since the respiratory exchange ratio (RER) is the ratio of $\dot{V}CO_2$ to $\dot{V}O_2$, that ratio will also be seen to increase, often to values greater than 1.

Individualized training programs must satisfy the basic goals of safety and effectiveness. Safety dictates that exercise be formed at the minimum effective heart rate whereas effectiveness dictates that the exercise program must result in the accomplishment of a desired goal, such as fat loss and improved cardiovascular fitness. In the past, many health professionals and some exercise equipment manufacturers use the so-called Karvonen method for determining what the heart rate should be during the exercise program if either fat burning or cardiovascular conditioning is the desired goal. In accordance with the Karvonen method, to determine the target heart rate to be maintained during a period of exercise to enhance fat burning, the following formula is commonly used:

Target heart rate = 220 − age − 0.6 × resting pulse rate + resting pulse rate

Likewise, for cardiovascular conditioning in accordance with the Karvonen method, the following formula is utilized:

Target heart rate = 220 − age − 0.8 × resting pulse rate

Use of the above formulas generally results in target heart rates which are too high to achieve fat reduction or higher than necessary to achieve improvements in cardiovascular fitness. Higher than necessary intensity of exercise, of course, impacts not only safety and efficacy, but also compliance. Because the high intensity of exercise results in the painful accumulation of lactate and depletion of muscle glycogen, individuals will not be able to comply with programs which specify high work intensities, such as those specified using the Karvonen predicted heart rates and exercise will be discontinued without achieving the desired goal.

When one exercises, there are several requirements which must be met in order for the exercising muscles to perform work. At low levels of exercise, such as walking at a modest rate, the exercising muscle must have oxygen and fuel to produce energy. The two types of fuels are fats and carbohydrates. The intensity of exercise dictates which fuel will be utilized during any type of exercise. Since carbohydrates tend to be a substantially more efficient fuel, it is the body's carbohydrates that are consumed during exercise at higher levels of intensity. Fat, being a less efficient fuel, tends to be consumed by the body when exercising at relatively low levels of intensity. Therefore, if a person exercises at too high of a heart rate, fat burning objectives will not be realized.

By monitoring the Respiratory Exchange Ratio (RER), it is possible to determine which type of fuel is being utilized at any given time. It is found that the closer that the RER is to 0.7, the greater the fat utilization. Contrariwise, the higher the intensity of exercise, the greater is the utilization of carbohydrates. By simultaneously monitoring the RER and the heart rate, it becomes possible to clearly identify the heart rate at which fat is the preferred fuel. It is commonly found that in unfit individuals, this is often at a surprisingly low level of work. In more fit individuals, fat will continue to be used as a fuel for longer periods. While exercise at a intense rate may cause a temporary weight loss due to a reduction in body water from sweating, we have determined that an exercise program designed to maximize the elimination of fat should be based upon activities and exercise where the heart rate is confined to a zone corresponding to the heart rate at a computed fat burning point ±10%. The fat burning point is computed as the valley in the RER curve or the lowest point where the respiratory exchange ratio is determined to be less than 0.90 and oxygen consumption is less than 55% of the peak oxygen uptake.

We have determined that for optimum cardiovascular improvement, exercise should be maintained in a zone such that the heart rate is maintained at the value at the anaerobic threshold plus 20%. While carbohydrates would be the fuel that is exclusively utilized at levels of exercise in this latter zone, there still exists certain benefits even for those desiring to lose fat. By improving cardiovascular fitness, the basal metabolic rate for the individual will increase. By increasing the basal metabolic rate, the number of calories that an individual routinely uses in activities of daily life increases. Interestingly, daily activities typically fall into the low intensity category in which fat is used as a fuel. So, by performing this higher intensity training on a regular basis, it is possible to improve fitness and have positive impact on fat loss.

In the Anderson et al. U.S. Pat. No. 4,463,764, there is described a computerized exercise testing system which allows a breath-by-breath analysis of the kinetics of $O_2$ uptake, $CO_2$ output and minute ventilation on a real-time basis during exercise. Using that equipment, it is possible to compute the respiratory exchange ratio and, from that, to determine the range of heart rates to be maintained during exercise if fat consumption is the goal. Moreover, that same equipment may be used to determine the anaerobic threshold and the heart rate existing at that point. Thus, using this data, the invention is able to compute the range of heart rates or work rates for enhancing fat loss and cardiopulmonary performance.

SUMMARY OF THE INVENTION

The present invention is concerned with a method for prescribing an exercise regimen for a subject to enhance fat burning and cardiovascular fitness by first providing a microprocessor-based, cardiopulmonary exercise system of the type including means for sensing respiratory flow of a subject and for measuring the resulting oxygen uptake, $\dot{V}O_2$, and carbon dioxide production, $\dot{V}CO_2$, on a breath-by-breath basis, means for sensing a pulse rate of a subject and means for measuring the work performed by the subject during a course of exercise. The subject is then subjected to a ramping cardiopulmonary stress test while using the microprocessor-based cardiopulmonary exercise system to measure and compute physiologic events correlating fat burning and cardiovascular fitness to heart rate or work rate and then providing the subject with a target heart rate range or work rate range for purposes of self-monitoring for adherence to an activity protocol, the activity protocol establishing a frequency for exercise sessions, a length of time for each of the exercise sessions and an intensity level of exercise during the exercise sessions as determined from an actual heart rate or work rate to be measured during each of the sessions. Where fat consumption is the goal, the physiological events correlating fat burning and cardiovascular fitness to heart rate involves computing the subject's respiratory exchange ratio and his peak $\dot{V}O_2$ and locatin the point where the RER is less than 90% and the oxygen uptake is less than 55% of its peak value. A heart rate or work rate range is then determined by noting the heart rate or work rate at the fat burning point and adding and subtracting 10% from that value.

For enhanced cardiovascular performance, the microprocessor-based exercise system determines the subject's anaerobic threshold and then sets the heart rate or work rate range at the heart rate at the anaerobic threshold at the lower end plus 20% of that rate at the upper end.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which.

DESCRIPTION OF THE PREFERRED EMBODIMENT

Figure 1:
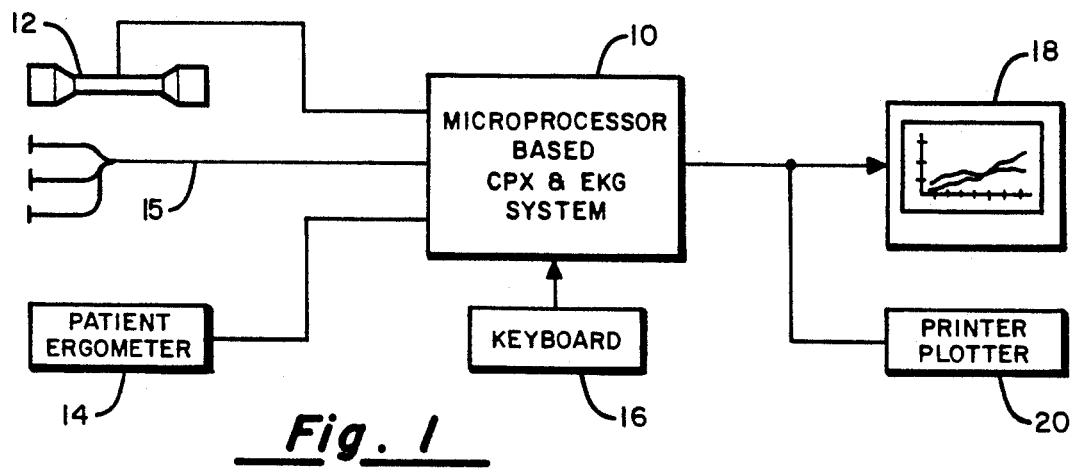
FIG. 1 is a system block diagram of the apparatus employed in carrying out the method of the present invention.

FIG. 1 illustrates a system block diagram of the apparatus employed in carrying out the method of the present invention. It is seen to comprise a microprocessor-based cardiopulmonary exercise and EKG system 10 which may include the System 2000 produced and sold by Medical Graphics Corporation of St. Paul, Minn., and which is more particularly described in the Anderson et al. U.S. Pat. No. 4,463,764. That patent is hereby incorporated by reference. This system, as well as more recently introduced Medical Graphics Corporation products, such as its CPX/D Cardiopulmonary Exercise System and its CardiO₂ ™ System may be used as well. Each includes a computer and a microprocessor-based waveform analyzer and they are adapted to receive respiratory flow information, via a subject's mouthpiece pneumotach 12, work-related data, via a subject's ergometer 14, and EKG information, via a conventional twelve-lead hookup 15 to electrodes appropriately positioned on the subject's body. Various operands, such as subject's I.D., subject's age, weight, height, etc. may be entered into the computer, via the keyboard 16. The equipment 10 is able to output a variety of parameters for real-time display on a CRT device 18. Also, hard copy can be obtained via a suitable printer/plotter 20.

In use, a subject will have a plurality of EKG electrodes appropriately attached on his/her body and will have the pneumotach mouthpiece 12 positioned in the mouth as different levels of work are performed on the subject's ergometer. The ergometer may typically be a stationary bicycle, a treadmill, a stair step or other suitable device. As the subject's exercise level increases, so too will heart rate and respiratory activity. The equipment shown in FIG. 1 will allow the storage and display of EKG signals picked up on the various leads 15, as well as gas exchange trend graph information showing real time, breath-by-breath data. The waveform analyzer contained within the device 10 permits oxygen and carbon dioxide gas samples to be drawn and $\dot{V}O_2$ and $\dot{V}CO_2$ data to be computed. The manner in which the respiratory-related data and the cardiac information is processed is more particularly described in the aforereferenced Anderson et al. U.S. Pat. No. 4,463,764.

Figure 2:
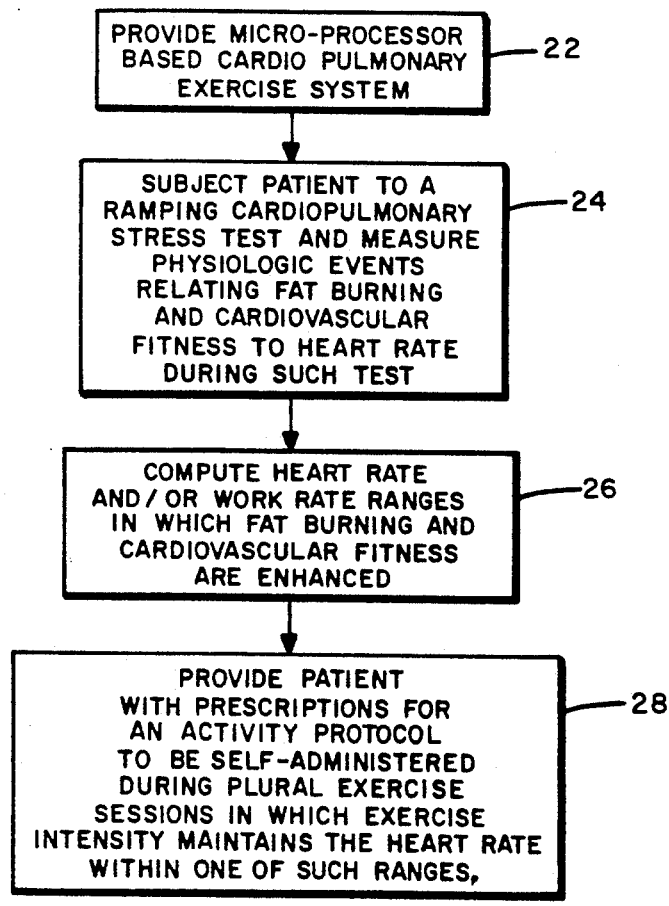
FIG. 2 is a process flow chart depicting the steps employed in determining target heart rate ranges for enhancing fat burning and cardiovascular fitness.

The basic steps of the method of the present invention are set out in the process flow chart of FIG. 2. As is indicated by block 22, in carrying out the method, the apparatus of FIG. 1 is first provided. With that equipment in place, and as reflected by block 24, the next step in the process is to subject a subject to a ramping cardiopulmonary stress test where the workload to which the subject is subjected is periodically increased. While the subject is being exercised, the equipment of FIG. 1 is used to measure physiologic events relating fat burning and cardiovascular fitness to heart rate. As those skilled in the art appreciate, in normal testing, physiologic response to increasing work is an increase in the subject's RER which, as already mentioned, is the ratio of $\dot{V}O_2$ and $\dot{V}CO_2$. It has been found that optimal fat utilization occurs when the RER is at its lowest value less than 0.90. Similarly, the physiological event determining the onset of cardiovascular improvement has been determined to occur at the subject's anaerobic threshold. All the while that the stress test is in progress, EKG information is stored in the microprocessor and from that information, heart rate and work rate during each point in the exercise schedule can be determined.

As reflected by block 26 in FIG. 2, the system of FIG. 1 is made to compute heart rate and work rate ranges in which fat burning and cardiovascular fitness are enhanced. The heart rate or work rate range in which fat burning is maximized is achieved by determining the heart rate at a "fat burning point" and then establishing the range as the heart rate at that fat burning point ±10 percent of that heart rate or the corresponding work rate. The heart rate or work rate range in which cardiovascular fitness is enhanced is determined by finding the subject's heart rate at his/her anaerobic threshold and then adding 20 percent to that heart rate or the corresponding work rate. The manner in which the fat burning point and the anaerobic threshold values are determined will be further explained hereinbelow.

As reflected by block 28, the professional conducting the stress test will provide the subject with prescriptions for an activity protocol to be self-administered during plural exercise sessions in which exercise intensity maintains the heart rate within one of the two ranges, the particular range being determined by whether the goal of the exercise session is to consume fat or to improve cardiovascular fitness.

Figure 3:
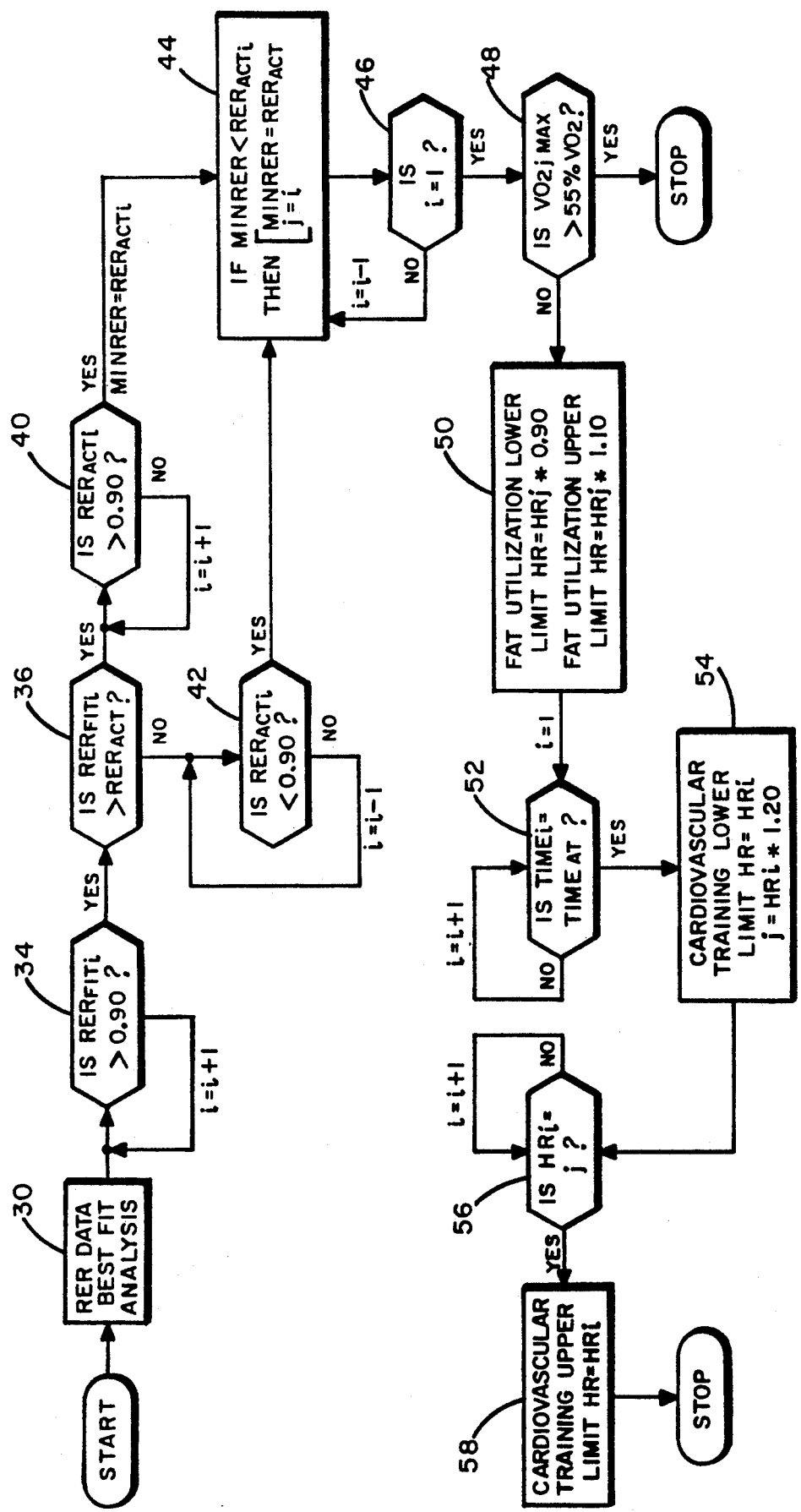
FIG. 3 is a software flow diagram of the algorithm employed in determining the heart rate ranges for enhancing fat loss during exercise and for improving cardiovascular fitness.

Referring now to FIG. 3, there is shown a software flow diagram depicting the algorithm employed in computing the ranges for the fat burning zone and for the cardiovascular training zone. The operations and tests depicted in this diagram are carried out after the stress test has been completed and the breath-by-breath measurements of $\dot{V}O_2$ and $\dot{V}CO_2$ and the associated EKG data have been sampled and stored in the memory of the microprocessor 10 of FIG. 1.

Figure 4:
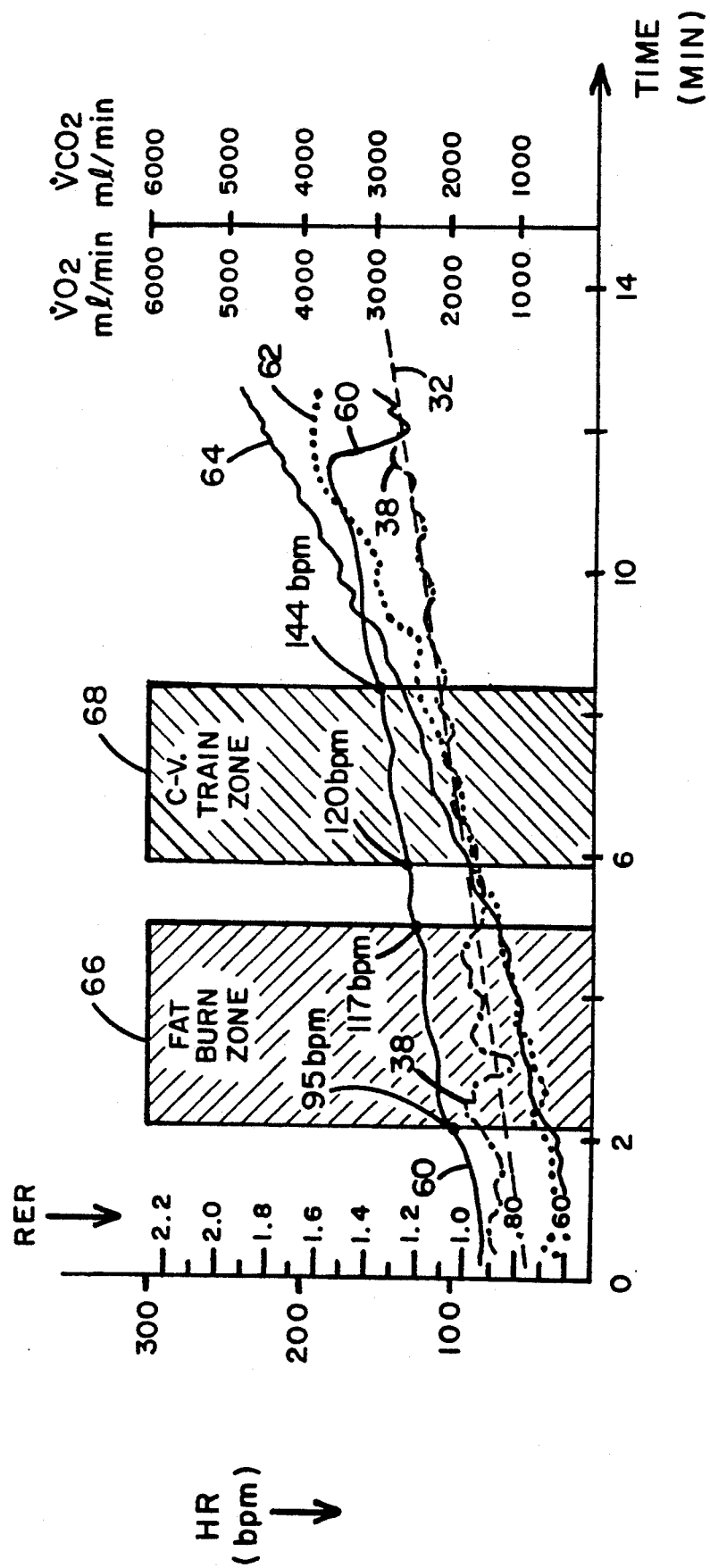
FIG. 4 is a graph illustrating a typical weight loss exercise prescription developed using the method of the present invention.

The computational process starts with a best fit analysis performed on the computed RER data. That is to say, RER is computed for each breath and then a curve fitting technique, such as a conventional linear regression or a exponential fit is carried out on the data so that a specific trend in the data can be obtained. In the graph of FIG. 4, the RER best fit curve is identified by numeral 32 and is seen to be generally linear with a predetermined positive slope.

The starting point for the search of the RER "valley" is determined by using the data from the best fit analysis to find a time, $T_1$, where the best fit RER is equal to 0.90. At decision block 34, a test is made to determine if the computed best fit RER for each breath is greater than 0.90. If it is not, the breath count is incremented and the test is repeated for the next successive breath. When it is found that the best fit RER has become greater than 0.90, a test is made at block 36 to determine whether the best fit RER for that breath exceeds the actual RER. In FIG. 4, the actual RER is represented by the curve 38 which is seen to vary about the best fit trend line 32. IF the test made at decision block 36 is positive, thereby indicating that the actual RER at time, $T_1$, is less than 0.90, the algorithm searches forward in time through the test data to find a time, $T_2$, where the actual RER is equal to 0.90 (block 40). However, if the actual RER at time, $T_1$, is greater than 0.90, the algorithm searches backward in time through the test data to find the time, $T_2$, that actual RER equals 0.90 (decision block 42).

Once the time, $T_2$, has been found, the algorithm again searches backwards in time through the test data to find a time, $T_3$, where the actual RER is a minimum. This is the result obtained when the operation and test identified by blocks 44 and 46 are repeated on an iterative basis.

Irrespective of the path taken from either decision block 40 or decision block 42, when it is determined that the current RER is less than the RER sample for the previous breath, the current minimum RER is retained and this operation is repeated until the backward counting test at the decision block 46 indicates that all of the breaths in the test have been examined. This, of course, results in locating the "valley" or low point in the actual RER curve 38 (FIG. 4).

Once the minimum RER breath time is located, a further test is made at block 48 to determine whether the oxygen uptake $\dot{V}O_2$ is greater than 55 percent of the maximum $\dot{V}O_2$ measured during the test sequence. If it is, the algorithm terminates and an error message is presented on the display. Assuming that the $\dot{V}O_2$ value at the time, $T_3$, where the actual RER is a minimum is less than 55 percent, the operation performed at block 50 is carried out. It is here that the range for the fat burning zone is established. In particular, the heart rate existing at the $T_3$ point is established and the lower limit of the heart rate zone is made equal to 90 percent of the heart rate existing at the $T_3$ point. Likewise, the upper limit for the zone is set at 110 percent of the heart rate at the $T_3$ point. The corresponding work rate is also noted.

In establishing the zone boundaries for the cardiovascular training zone, the exercise test data read from the memory of the computer is examined and the anaerobic threshold is located. The particular breath that is extant at the point where the anaerobic threshold is reached is also known, as is the heart rate existing at that moment. The test identified by block 52 in FIG. 3 locates the particular time at which the anaerobic threshold is reached and, as indicated by block 54, the heart rate at the anaerobic threshold is read out. The lower boundary for the cardiovascular training zone is set at the heart rate at the anaerobic threshold. The upper limit for the cardiovascular training zone is set at 120 percent of the heart rate at the anaerobic threshold. The decision block 56 is used to successively examine the heart rate data to determine the value when 120 percent of the lower limit heart rate is present and the operation block 58 sets that value as the upper limit. At this point the algorithm is completed and a printout of the exercise prescription can be displayed and printed out. The corresponding work rate at these boundaries are also noted and may be used as the zone boundaries.

Referring again to FIG. 4, there is shown a plot of heart rate in beats-per-minute (curve 60), oxygen uptake in milliliters-per-minute (curve 62) and $\dot{V}CO_2$ (curve 64). This plot shows actual data taken on a 35 year old male, 6 ft. tall and weighing 200 pounds. The fat utilization zone is defined by the rectangular block 66 and the cardiovascular training zone is bounded by the block 68

The exercise prescription utilizes heart rate or corresponding work rate as a marker which one can use to optimize fat loss and/or cardiovascular conditioning during a series of exercise sessions. By maintaining the heart rate between a lower limit of 94 beats-per-minute and an upper limit of 117 beats-per-minute or work rate of between 1 and 89 watts, this individual will maximize fat loss. Likewise, by maintaining a heart rate in a zone between 120 beats-per-minute and 144 beats-per-minute or work rate of 109-182 watts, cardiovascular training is optimized.

For the individual whose data is that set out in FIG. 4, for fat loss, he should exercise at a low intensity (walking), perhaps four times per week for greater than 45 minutes during each such session while monitoring his heart rate to make sure that it resides in the fat utilization zone 66. For improved cardiovascular performance, the subject should exercise by running, walking or cycling, again four times per week for more than 20 minutes a day at a heart rate maintained between 120 beats-per-minute and 144 beats-per-minute.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for prescribing an exercise regimen for a subject to enhance one of fat consumption and cardiovascular fitness comprising the steps of:
    (a) providing a microprocessor-based cardiopulmonary exercise system of the type including means for sensing respiratory flow of a subject while undergoing exercise of predetermined intensity levels and for measuring the resulting oxygen uptake $\dot{V}O_2$) and carbon dioxide production ($\dot{V}CO_2$) on a breath-by-breath basis, means for sensing a pulse rate of said subject and means for measuring the work performed by said subject during a plurality of stages of exercise;
    (b) subjecting said subject to a ramping cardiopulmonary stress test while using said microprocessor-based cardiopulmonary exercise system to measure and compute physiologic events correlating fat burning and cardiovascular fitness to heart rate; and
    (c) providing said subject with a target heart rate range or work rate range for purposes of self-monitoring for adherence to an activity protocol, said activity protocol establishing a frequency for exercise sessions, a length of time for each of said exercise sessions and an intensity level of exercise during said exercise sessions as determined from an actual heart rate or work rate to be measured during each of said exercise sessions.

2. The method as in claim 1 wherein said physiologic events correlating fat burning and cardiovascular fitness to heart rate or work rate comprises computing the subject's respiratory exchange ratio (RER).

3. The method as in claim 2 wherein said target heart rate range is computed by the steps of:
    (a) determining the subject's heart rate at a fat burning point; and
    (b) setting said heart rate range at said heart rate at a fat burning point plus or minus ten percent of said heart rate at a fat burning point.

4. The method as in claim 3 wherein said fat burning point is determined by the steps of:
    (a) locating the lowest point where the RER is less than 0.90 and the oxygen uptake is less than 55 percent of a measured peak value of $\dot{V}O_2$.

5. The method as in claim 2 wherein said target heart rate is determined through the steps of:
    (a) using said microprocessor-based cardiopulmonary exercise system to determine the subject's heart rate at said subject's anaerobic threshold; and
    (b) adding 20 percent to said heart rate at said anaerobic threshold.

* * * * *